US010653361B2

(12) United States Patent
DeBates et al.

(10) Patent No.: US 10,653,361 B2
(45) Date of Patent: May 19, 2020

(54) BREATH SENSORY ON A MOBILE COMMUNICATION DEVICE

(71) Applicant: Motorola Mobility LLC, Chicago, IL (US)

(72) Inventors: Scott Patrick DeBates, Crystal Lake, IL (US); Douglas Alfred Lautner, Round Lake, IL (US)

(73) Assignee: Motorola Mobility LLC, Chicago, IL (US)

(*) Notice: Subject to any disclaimer, the term of this patent is extended or adjusted under 35 U.S.C. 154(b) by 309 days.

(21) Appl. No.: 15/599,275

(22) Filed: May 18, 2017

(65) Prior Publication Data
US 2018/0333101 A1   Nov. 22, 2018

(51) Int. Cl.
| | | |
|---|---|---|
| *H04M 1/21* | (2006.01) |
| *G08B 21/18* | (2006.01) |
| *A61B 5/00* | (2006.01) |
| *A61B 5/08* | (2006.01) |
| *A61B 10/00* | (2006.01) |
| *A61B 5/097* | (2006.01) |

(52) U.S. Cl.
CPC ............ *A61B 5/6898* (2013.01); *A61B 5/082* (2013.01); *A61B 5/097* (2013.01); *A61B 10/00* (2013.01); *A61B 5/0022* (2013.01); *A61B 2010/0009* (2013.01); *A61B 2010/0087* (2013.01); *A61B 2560/0242* (2013.01); *H04M 1/21* (2013.01); *H04M 2250/12* (2013.01)

(58) Field of Classification Search
CPC .. A61B 5/00; A61B 5/08; H04M 1/21; H04M 1/72522; H04M 2250/12; H04M 1/72527; G08B 21/18; G01N 33/0062; G01N 33/0036; G01N 33/4972; G01N 2033/497
See application file for complete search history.

(56) References Cited

U.S. PATENT DOCUMENTS

| | | | | |
|---|---|---|---|---|
| 6,858,182 B1* | 2/2005 | Ito | ........................ | G01N 33/497 340/870.28 |
| 8,224,608 B1* | 7/2012 | Son | ..................... | G01N 33/4972 702/104 |
| 8,323,206 B2* | 12/2012 | Castrodale | ............. | A61B 5/097 436/132 |
| 9,299,238 B1* | 3/2016 | Ahmad | ................. | A61B 5/4833 |
| 9,312,713 B2* | 4/2016 | Graf | .................. | G01N 33/48785 |
| 9,486,169 B1* | 11/2016 | Ahmad | ................. | A61B 5/6898 |
| 9,772,317 B2* | 9/2017 | Mayer | ................ | G01N 33/0006 |

(Continued)

OTHER PUBLICATIONS

"Notice of Allowance", U.S. Appl. No. 15/599,343, dated Oct. 17, 2019, 10 pages.

(Continued)

*Primary Examiner* — Mohammad K Islam
(74) *Attorney, Agent, or Firm* — SBMC

(57) ABSTRACT

Various embodiments provide a mobile communication device, such as a mobile communication device, with functions including telecommunications capabilities, breath sensory functions and, in some instances, environmental air sensing functions. The breath sensory functions can be used to measure alcohol levels, as well as to detect properties that pertain to various health conditions and issues. The environmental air sensing functions can, in at least some embodiments, be provided along with the breath sensory functions.

20 Claims, 10 Drawing Sheets

(56) References Cited

U.S. PATENT DOCUMENTS

| | | | |
|---|---|---|---|
| 10,241,105 B2* | 3/2019 | Kwak | A61B 5/082 |
| 10,491,729 B2 | 11/2019 | Debates et al. | |
| 2007/0093725 A1* | 4/2007 | Shaw | A61B 5/097 600/543 |
| 2008/0146892 A1* | 6/2008 | LeBoeuf | G16H 50/30 600/300 |
| 2010/0012417 A1* | 1/2010 | Walter | B60K 28/063 180/272 |
| 2010/0063408 A1* | 3/2010 | Nothacker | G01N 33/4972 600/532 |
| 2010/0234064 A1* | 9/2010 | Harris, Jr. | B60K 28/066 455/556.1 |
| 2011/0309932 A1* | 12/2011 | Arringdale | B60K 28/063 340/539.14 |
| 2012/0157871 A1* | 6/2012 | Walden | A61B 5/097 600/532 |
| 2012/0232419 A1* | 9/2012 | Chazan | G01N 21/783 600/532 |
| 2013/0021153 A1* | 1/2013 | Keays | G01N 33/4972 340/539.12 |
| 2013/0035602 A1* | 2/2013 | Gemer | A61B 5/0404 600/484 |
| 2013/0150746 A1* | 6/2013 | Tao | G06Q 50/22 600/531 |
| 2013/0344609 A1* | 12/2013 | Mayer | G01N 33/497 436/133 |
| 2014/0004908 A1* | 1/2014 | Park | H04W 88/02 455/566 |
| 2014/0016668 A1* | 1/2014 | Boni | G06F 3/017 374/143 |
| 2014/0055346 A1* | 2/2014 | Boni | H03K 17/94 345/156 |
| 2014/0076022 A1* | 3/2014 | Ohlsson | G01N 33/4972 73/23.3 |
| 2014/0141761 A1* | 5/2014 | Yun | H04M 1/72569 455/418 |
| 2014/0216136 A1* | 8/2014 | Yim | G01N 33/4972 73/31.05 |
| 2014/0228651 A1* | 8/2014 | Causevic | A61B 5/0402 600/301 |
| 2014/0377877 A1* | 12/2014 | Burgi | G01N 33/4972 436/120 |
| 2015/0182146 A1* | 7/2015 | Hidaka | G01N 33/497 455/418 |
| 2015/0196251 A1* | 7/2015 | Outwater | A61B 5/4875 600/301 |
| 2015/0233897 A1* | 8/2015 | Hok | G01N 33/4972 73/23.3 |
| 2016/0103966 A1* | 4/2016 | Mirza | G06Q 30/04 705/2 |
| 2016/0150995 A1* | 6/2016 | Ratto | A61B 5/0022 600/532 |
| 2016/0161468 A1* | 6/2016 | Keays | G01N 33/4972 73/23.3 |
| 2016/0317074 A1* | 11/2016 | Kawai | A61B 5/7405 |
| 2016/0325058 A1* | 11/2016 | Samson | G16H 40/67 |
| 2016/0361678 A1 | 12/2016 | Blackley | |
| 2016/0371590 A1* | 12/2016 | Blackley | G06N 5/04 |
| 2017/0032787 A1* | 2/2017 | Dayal | A61H 3/061 |
| 2017/0074857 A1* | 3/2017 | Dennis | A61B 5/0836 |
| 2017/0119279 A1* | 5/2017 | Ahmad | A61B 5/74 |
| 2017/0176411 A1* | 6/2017 | Trainor | G01N 33/4972 |
| 2017/0188864 A1* | 7/2017 | Drury | A61B 5/0408 |
| 2017/0212100 A1* | 7/2017 | Kwak | A61B 5/082 |
| 2017/0246486 A1* | 8/2017 | Cazier | A62B 27/00 |
| 2017/0318135 A1* | 11/2017 | Han | H04M 1/0202 |
| 2017/0333638 A1* | 11/2017 | Kondoh | A61M 5/20 |
| 2017/0336388 A1* | 11/2017 | Keays | G01N 33/4972 |
| 2017/0350877 A1* | 12/2017 | Keays | A61B 5/082 |
| 2017/0361133 A1* | 12/2017 | Yu | F04D 25/084 |
| 2018/0074029 A1* | 3/2018 | DeVries | G01N 33/4972 |
| 2018/0075219 A1* | 3/2018 | Klein | G06F 19/34 |
| 2018/0338023 A1 | 11/2018 | DeBates et al. | |

OTHER PUBLICATIONS

"Non-Final Office Action", U.S. Appl. No. 15/599,343, dated May 24, 2019, 22 pages.

* cited by examiner

BREATH SENSORY ON A MOBILE COMMUNICATION DEVICE

BACKGROUND

As technology continues to advance, challenges are posed to those who develop and manufacture mobile devices to continue to provide better and different technology options to consumers.

BRIEF DESCRIPTION OF THE DRAWINGS

Embodiments for breath sensory and environmental sensing are described with reference to the following Figures. The same numbers may be used throughout to reference like features and components that are shown in the Figures.

DETAILED DESCRIPTION

Overview

Figure 1:
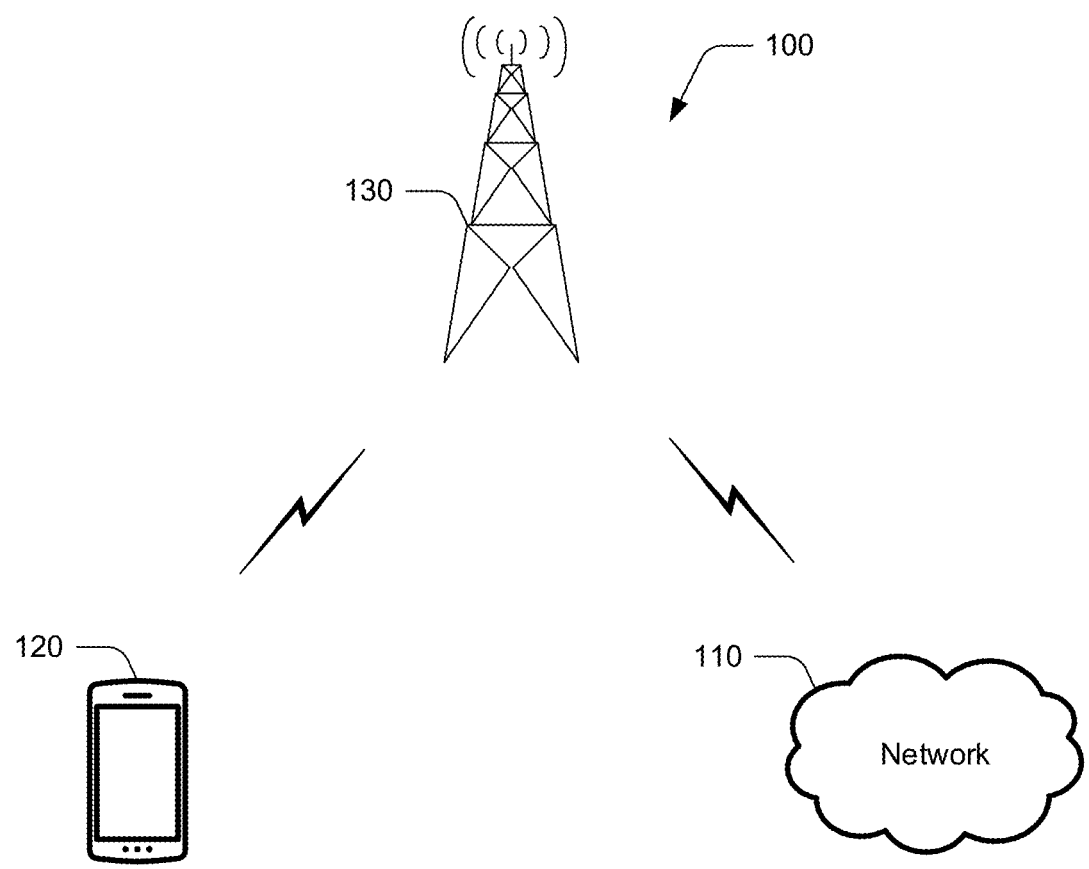
FIG. 1 illustrates an example operating environment in accordance with one or more embodiments.

Various embodiments provide a mobile communication device with functions including telecommunications capabilities, breath sensory functions and, in some instances, breath sensory and environmental air sensing functions. Mobile communication devices include, by way of example and not limitation, smart phones, smart devices, IoT (Internet of Things) devices such as wearables such as smart watches, and the like. The breath sensory functions can be used to measure alcohol levels, as well as to detect properties that pertain to various health conditions and issues. The environmental air sensing functions can, in at least some embodiments, be provided along with the breath sensory functions. In at least some embodiments, the environmental air sensing functions and the breath sensory functions can be selected by a user. For example, the user may opt to enable the breath sensory functions and then, may opt to switch to the environmental air sensing functions. In other embodiments, the environmental air sensing functions and the breath sensory functions can be automatically selected depending on a context associated with the mobile communication device. That is, the mobile communication device can determine a particular context, such as whether or not the user is on a telephone call, and can automatically select and enable the breath sensory functions. Alternately, the mobile communication device can determine when the user is not on a telephone call and the mobile communication device is in a state in which the environmental air sensing functions can be enabled. In these instances, the environmental air sensing functions can be automatically selected and enabled by the device. Of course, the user can be provided with a notification that the environmental air sensing functions are available and can be given the choice as to whether enable the functions or not.

In at least some embodiments, sensors and related componentry that implement the breath sensory functions and environmental air sensing can be integrated as part of the mobile communication device. That is, such sensors and related componentry can be included within the housing and can comprise an integral part of the mobile communication device. Alternately or additionally, such sensors and related componentry can be included in a modular attachment which may be detachably connected to the mobile communication device. In these instances, the modular attachment can communicate with the mobile communication device through a suitably-configured hardware interface.

The various embodiments described herein thus provide a robust collection of functionality contained in a mobile device. By including breath sensory functionality and, in some embodiments, environmental air sensing functionality, the embodiments can promote the health and physical fitness of the user by enabling the user to gather timely data and information concerning the air that they breathe. In at least some instances, the data and information gathered by the mobile device can be provided to a third-party service provider for further analysis and evaluation. Results of the analysis and evaluation can be conveyed back to the mobile device and the user can be notified of the results. This can greatly reduce the amount of time that a user must wait for an evaluation and the associated results.

While features and concepts for breath sensory and environment sensing can be implemented in any number of different devices, systems, environments, and/or configurations, embodiments for breath sensory and environment sensing are described in the context of the following example devices, systems, and methods.

Example Operating Environment

FIG. 1 is an example block diagram of a system 100 according to one or more embodiments. The system 100 can include a network 110, a terminal 120, and a base station 130. The terminal 120 may be a wireless communication device, such as a mobile communication device, a personal digital assistant, and the like. The network 110 may include any type of network that is capable of sending and receiving signals, such as wireless signals. For example, the network 110 may include a wireless telecommunications network, a cellular telephone network, a Time Division Multiple Access (TDMA) network, a Code Division Multiple Access (CDMA) network and other like communications systems. In operation, the terminal 120 can communicate with the network 110 and with other devices on the network 110 by sending and receiving wireless signals via the base station 130.

Mobile Communication Device with Portable Breath Analyzer

Figure 2:
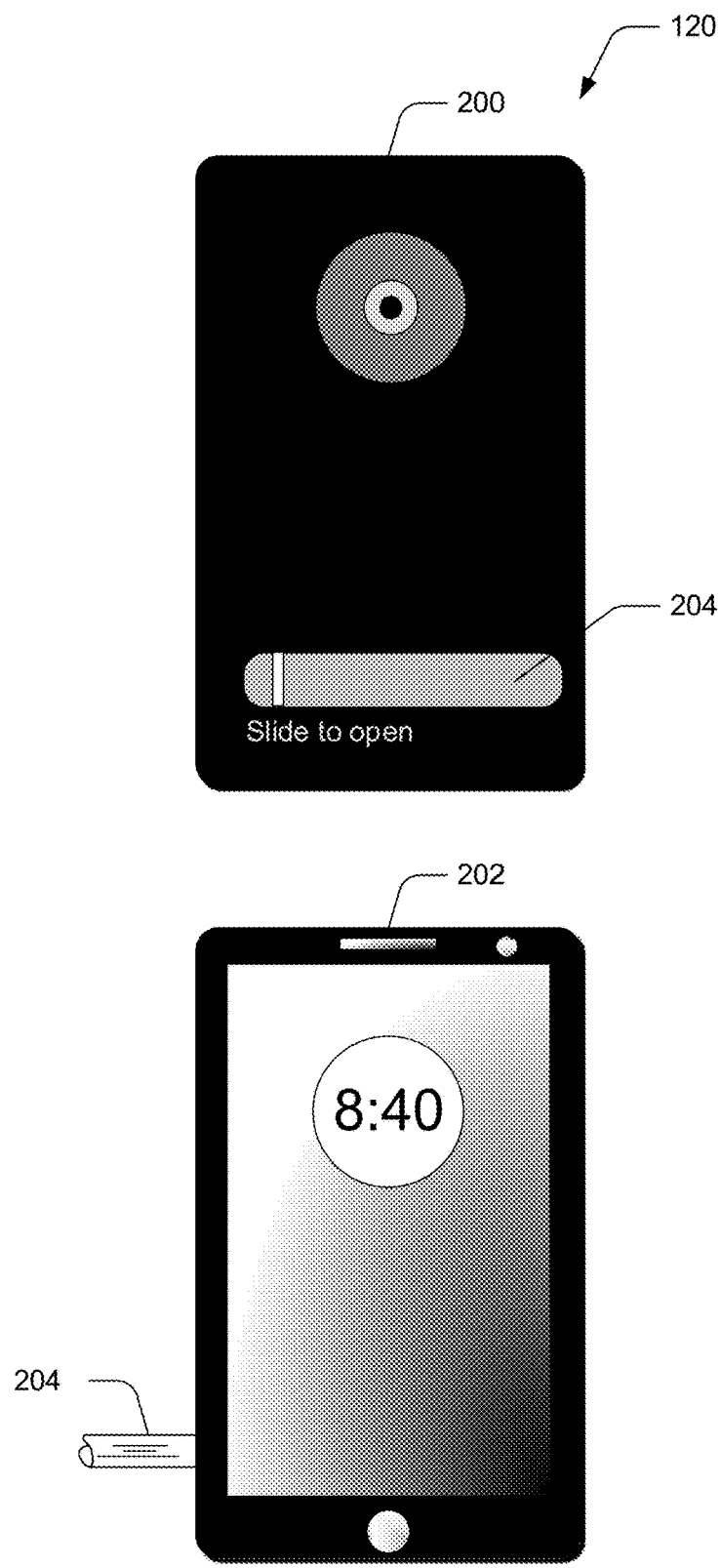
FIG. 2 illustrates an example terminal in the form of a mobile communication device in accordance with one or more embodiments.

FIG. 2 illustrates an example terminal 120 in the form of a mobile communication device. A view of the backside of the mobile communication device is shown at 200, and a view of the front side of the mobile communication device is shown at 202. The mobile communication device 120 includes a slidably deployable tube 204 that forms part of a breath analysis module. In the backside view 200, the deployable tube 204 is shown in an un-deployed position. In the front side view 202, the deployable tube 204 is shown in a deployed position. When deployed, a force sensor associated with the deployable tube can monitor PSI conditions internally of the tube to ascertain when the user is blowing into the tube. When the user blows into the deployable tube 204, components of the breath analysis module, either internal to the mobile communication device 120 or forming part of a modular attachment to the mobile communication device 120, can analyze the user's breath in one or more ways. For example, a user's breath can be analyzed for various health-related issues or potential health-related issues. For example, in at least some embodiments, the user's breath can be analyzed for various compounds. Such compounds can include, by way of example and not limitation, water, carbon dioxide, $H_2$, sulfides, ammonia, ethanol, aldehyde, acetone, and the like. The presence of these and other compounds can be indicative of health-related issues or potential health-related issues. Once detected, information or data describing the presence or absence of these compounds can be analyzed and reported to the user. Analysis can take place either on the mobile communication device 120 or remote from the mobile communication device, as by a third-party provider. In the latter instance, the information or data can be transmitted by the mobile communication device 120 over network 110 to the third-party provider. Once the third-party provider has analyzed the information or data, the results can then be reported back to the user and displayed on the mobile communication device 120.

Alternately or additionally, the user's breath can be analyzed for alcohol content. In addition, in at least some embodiments, the user's breath can be analyzed to ascertain whether the user has bad breath, also known as halitosis and fetor oris. Bad breath can be associated with depression and symptoms of obsessive-compulsive disorder. Bad breath can also occur due to disorders in the nose, sinuses, throat, lungs, kidneys, esophagus, or stomach. In some rare instances, bad breath can be due to an underlying medical condition such as liver failure or ketoacidosis. As in the above example, once detected, information or data describing the presence or absence of bad breath can be analyzed and reported to the user. Analysis can take place either on the mobile communication device 120 or remote from the mobile communication device, as by a third-party provider. In the latter instance, the information or data can be transmitted by the mobile communication device 120 over network 110 to the third-party provider. Once the third-party provider has analyzed the information or data, the results can then be reported back to the user and displayed on the mobile communication device 120. This can provide a valuable and timely diagnostic tool to enable the user to seek further medical attention in the event a bad breath condition is found.

In at least some embodiments, one or more subscription services can be offered by third-party providers. Thus, a user may enroll in a fee-based third-party service to have their breath analyzed by way of the breath analysis module and the third-party provider. Results can then be reported back by the third-party provider to the user.

Figure 3:
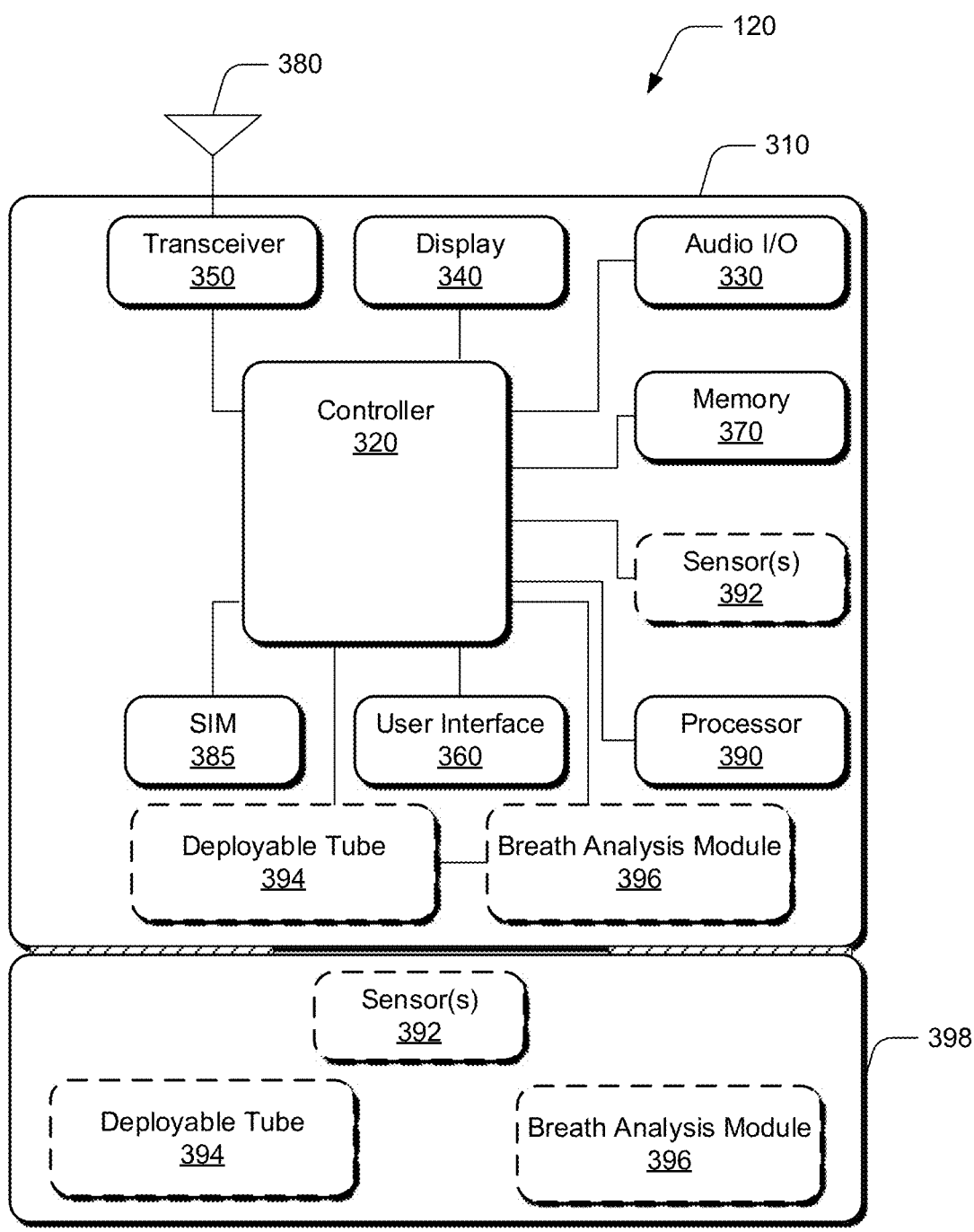
FIG. 3 illustrates a block diagram of an example mobile communication device in accordance with one or more embodiments.

FIG. 3 is an example block diagram of a mobile communication device 120 in accordance with one or more embodiments. The mobile communication device 120 can include a housing 310, a controller 320 coupled to the housing 310, audio input and output circuitry 330 coupled to the housing 310, a display 340 coupled to the housing 310, a transceiver 350 coupled to the housing 310, a user interface 360 coupled to the housing 310, memory 370, an antenna 380 coupled to the housing 310 and the transceiver 350, and a subscriber identification module 385 coupled to the controller 320. The mobile communication device 120 also includes a processor 390 connected to controller 320. The mobile communication device 120 depicted in FIG. 3 can be used to implement all the embodiments described in this document.

In addition, mobile communication device 120 can include or otherwise be operably connected to one or more sensors 392, a deployable tube 394 and a breath analysis module 396. The sensors, deployable tube, and breath analysis module are shown in dashed lines because, as noted above, the sensors 392, deployable tube 394, and breath analysis module 396 may optionally be internal to the mobile communication device 120. Alternately or additionally, these components may reside in a modular attachment, such as modular attachment 398, that is attached to the mobile communication device 120 and communicatively linked to components of the mobile communication device by way of a suitable interface, such as a hardware interface. An example modular attachment is Lenovo's Moto Mod, although other modular attachments may be employed.

Such modular attachment attaches to the mobile communication device using strong magnetic coupling elements, represented in the illustration as two crosshatched coupling elements between the housing 310 and modular attachment 398. A hardware interface (not specifically illustrated) between the modular attachment 398 and the mobile communication device 120 enables information and data to be exchanged between the modular attachment and the mobile communication device. So, for example, if sensors 392, deployable tube 394, and breath analysis module 396 reside in the modular attachment 398, information and data gathered by the modular attachment can be conveyed to the mobile communication device 120 by way of the hardware interface. This information and data can then, in at least some embodiments, be conveyed by the mobile communication device 120 to a third-party service provider for further analysis.

In the illustrated and described embodiment, the controller 320 is connected to various components within the mobile communication device 120 and is configured to organize, manage, and oversee processing that takes place on the mobile communication device. This includes serving as an interface to the various illustrated components to process information and data received from the components.

The audio input and output circuitry 330 can include a microphone, a speaker, a transducer, or any other audio input and output circuitry. The display 340 can be a liquid crystal display (LCD), a light emitting diode (LED) display, a plasma display, or any other means for displaying image and information. The transceiver 350 may include a transmitter and/or a receiver. The user interface 360 can include a hard or soft keypad, buttons, a touch pad, a joystick, an additional display, or any other device useful for providing an interface between a user and an electronic device. The memory 370 can include embedded memory such as a random access memory, a read only memory, etc. Memory 370 can include software code that is executable to implement various functionality on the mobile communication device.

The SIM 385 is an integrated circuit that stores information which is used to identify and authenticate subscribers on mobile telephony devices. It can also store contact information as well.

Processor 390 is configured to include a processing system of one or more processors (e.g., any of microprocessors, controllers, and the like) and/or a processor and memory system implemented as a system-on-chip (SoC) that processes computer-executable instructions. The processor system may be implemented at least partially in hardware, which can include components of an integrated circuit or on-chip system, an application-specific integrated circuit (ASIC), a field-programmable gate array (FPGA), a complex programmable logic device (CPLD), and other implementations in silicon and/or other hardware.

Sensors 392 can comprise any suitable type of sensors such as, by way of example and not limitation, breath alcohol sensors, bad breath sensors, $CO_2$ sensors, force sensors to sense a user's breath, such as when a user is blowing into the deployable tube 394, talking on the mobile communication device, sulfide sensors, acetone sensors, ammonia sensors, ethanol sensors, $H_2$ sensors and the like. In some embodiments, the sensors can also include humidity and temperature sensors. The humidity and temperature sensors can be used for calibrating other sensors before analyzing the user's breath and breath gases. That is, ambient humidity and temperature will have an effect on the various sensors in the mobile communication device 310. Accordingly, the humidity and temperature sensors are utilized to calibrate the other sensors before use. In these embodiments, when the user deploys the deployable tube 394, the humidity and temperature sensors can calibrate the gas baseline. When the user blows into the deployable tube, the difference or "delta" of the gas measured responsive to the user blowing into the tube can be computed. This can facilitate a more accurate measurement of the user's breath or breath gases because such measurement takes into account the ambient humidity and temperature. In other embodiments, such as those that perform environmental sensing functionality (described below), the humidity and temperature sensors can calibrate the gas baseline before analyzing the environmental ambient gases. This can be done, for example, before enabling a fan to pull in the ambient gases, as described below in more detail. The breath analysis module 396 can include any suitable type of breath analysis functionality.

Having considered an example mobile communication device and its components in accordance with one or more embodiments, consider now an example method in accordance with one or more embodiments.

Figure 4:
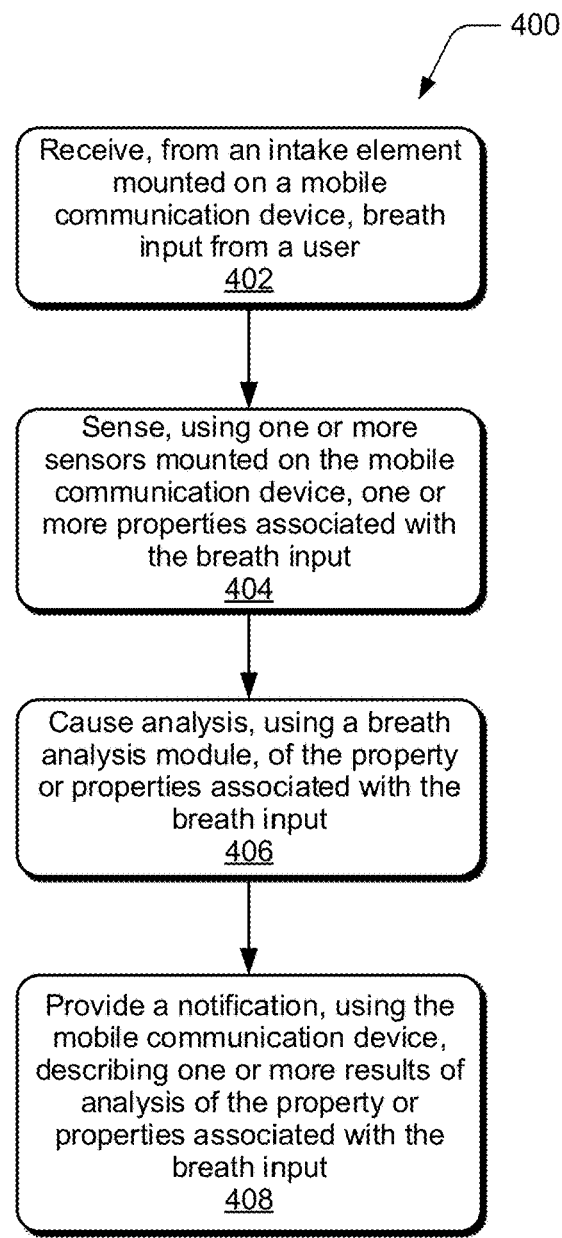
FIG. 4 is a flow diagram that illustrates operations in accordance with one or more embodiments.

FIG. 4 illustrates an example method 400 that employs breath sensory techniques, in connection with a mobile communication device, in accordance with one or more embodiments. Generally, any services, components, modules, methods, and/or operations described herein can be implemented using software, firmware, hardware (e.g., fixed logic circuitry), manual processing, or any combination thereof. Some operations of the example methods may be described in the general context of executable instructions stored on computer-readable storage memory that is local and/or remote to a computer processing system, and implementations can include software applications, programs, functions, and the like. Alternately or in addition, any of the functionality described herein can be performed, at least in part, by one or more hardware logic components, such as, and without limitation, Field-programmable Gate Arrays (FPGAs), Application-specific Integrated Circuits (ASICs), Application-specific Standard Products (ASSPs), System-on-a-chip systems (SoCs), Complex Programmable Logic Devices (CPLDs), and the like. The order in which the method is described is not intended to be construed as a limitation, and any number or combination of the described method operations can be performed in any order to perform a method, or an alternate method.

At 402, breath input from a user is received, from an intake element mounted on a mobile communication device. Prior to receiving the breath input, the sensors on the mobile communication device can be calibrated using the humidity and temperature sensors as described above. Any suitable intake element can be utilized. In at least one embodiment, the intake element comprises a slidably deployable tube that is mounted on the device. In at least some embodiments, the slidably deployable tube can be an integral part of the mobile communication device. In at least some other embodiments, the slidably deployable tube can be part of a modular attachment that is connected to the mobile communication device. The modular attachment can be connected at any suitable location on the mobile communication device. In at least some embodiments, the modular attachment is mounted to the backside of the mobile communication device and may be held in place by magnetic coupling elements. When so mounted, components within the modular attachment can communicate with components of the mobile communication device through a suitably-configured hardware interface.

At 404, one or more properties associated with the breath input are sensed using one or more sensors mounted on the mobile communication device. Any suitable property or properties can be sensed by any suitable type of sensors. For example, properties can include, by way of example and not limitation, the constituent parts contained within or composition of the breath. Such constituent parts can include compounds, volatile compounds, volatile organic compounds, molecules, and/or constituent parts that may pertain to health-related issues. For example, the presence of certain materials in a user's breath can be indicative of certain types of cancer, such as lung cancer, esophageal cancer, tongue cancer, colorectal cancer, and the like. Further, the properties of exhaled breath may contain valuable information for users presenting with asthma, renal and liver diseases, chronic obstructive pulmonary disease, inflammatory lung disease, or metabolic disorders. Furthermore, the properties of exhaled breath may include information pertaining to chemical markers, such as acetone, which may be indicative of type I diabetes. Furthermore, the properties may include information that pertains to conditions such as lactose intolerance, fructose intolerance, various allergies, and the like. Alternately or additionally, the property or properties can include alcohol content of the breath and/or whether the user's breath can be categorized as "bad breath."

Needless to say, there are simply hundreds if not thousands of potential conditions or issues that can be identified by way of the properties associated with a user's breath. The examples provided above are intended to serve as examples only, and are not intended to limit application of the claimed subject matter.

At 406, the property or properties associated with the breath input are caused to be analyzed using, in at least some instances, a breath analysis module mounted on the mobile communication device. In yet other instances, the property or properties associated with the breath input are caused to be analyzed by transmitting information or data associated with the property or properties to a third-party provider. This can be performed by transmitting the information or data to the third-party provider using the mobile communication device.

At 408, a notification describing one or more results of analysis of the property or properties associated with the breath input is provided. The notification can include any suitable type of information that might be useful for a user. For example, the notification may simply inform the user of factual information associated with the analysis, such as the particular composition making up the user's breath. Alternately or additionally, the notification may include further information such as diagnostic information, remedial information, or recommendations such as a recommendation to seek further medical assistance as a follow-up.

The notification can be a visual notification that is displayed by the mobile communication device. Alternately or additionally, the notification can be an audible notification. In embodiments where the breath analysis takes place locally on the mobile communication device, the notification can be provided directly by the mobile communication device itself or components of or associated with the mobile communication device. In embodiments where the breath analysis takes place remotely from the mobile communication device, as by a third-party provider, the notification can be provided by receiving information from the third-party provider and providing a notification that includes the information provided by the third-party provider.

Having considered an example mobile communication device with a portable breath analyzer, consider now a mobile communication device with a portable breath analyzer and environmental air sensing functionality.

Figure 5:
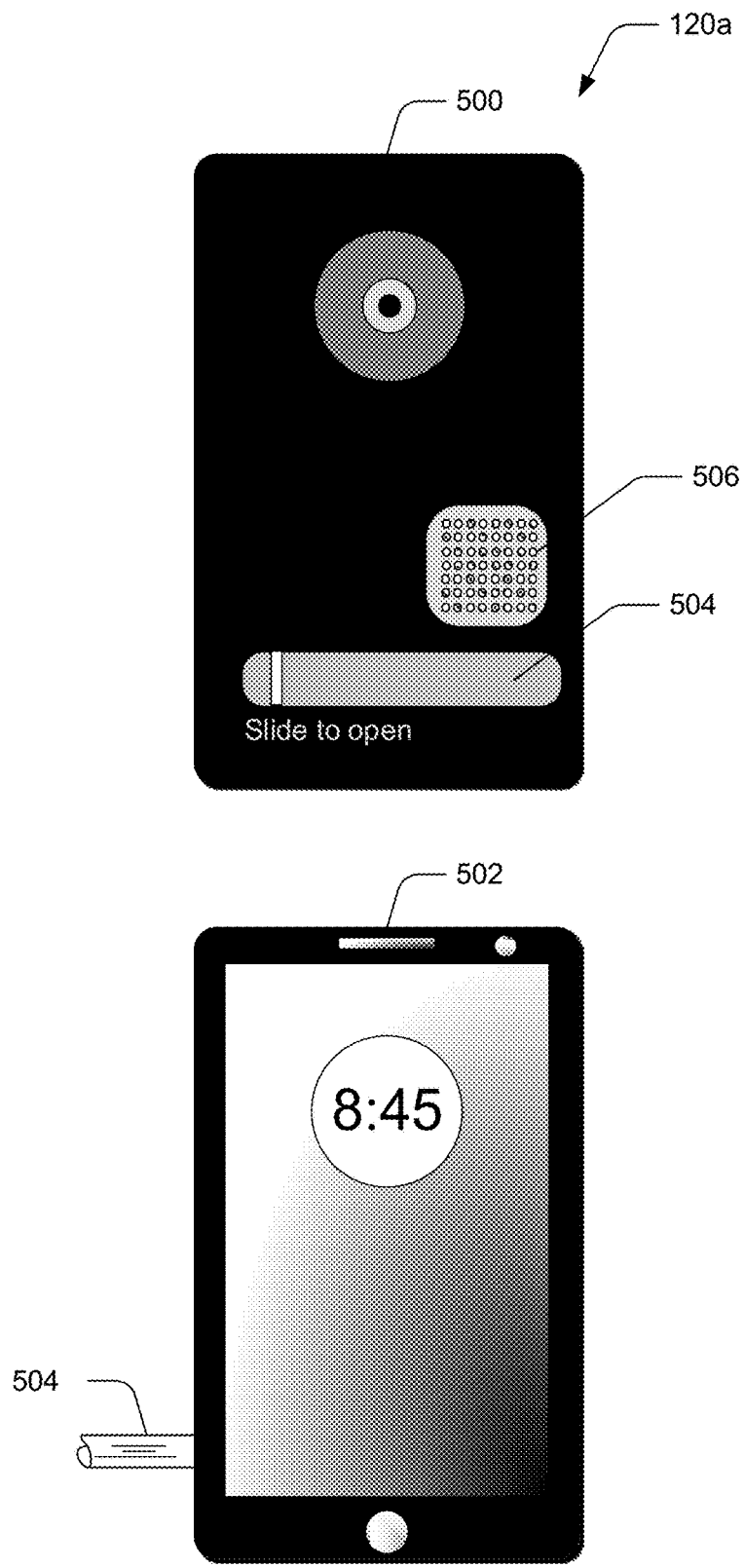
FIG. 5 illustrates an example terminal in the form of a mobile communication device in accordance with one or more embodiments.

Mobile Communication Device with Portable Breath Analyzer and Environmental Air Sensing Functionality FIG. 5 illustrates an example terminal 120a in the form of a mobile communication device in accordance with one or more embodiments. A view of the backside of the mobile communication device is shown at 500, and a view of the front side of the mobile communication device is shown at 502. The mobile communication device 120a includes a slidably deployable tube 504 that forms part of a breath analysis module, the same as or similar to that described above. In addition, the mobile communication device 120a includes an environment sensing inlet and fan 506.

In the backside view 500, the deployable tube 504 is shown in an un-deployed position. In the front side view 502, the deployable tube 504 is shown in a deployed position. When deployed, a force sensor associated with the deployable tube can monitor PSI conditions internally of the tube to ascertain when the user is blowing into the tube. When the user blows into the deployable tube 504, components of the breath analysis module, either internal to the mobile communication device 120a or forming part of a modular attachment to the mobile communication device 120a, can analyze the user's breath in one or more ways. For example, a user's breath can be analyzed for various health-related issues or potential health-related issues. For example, in at least some embodiments, the user's breath can be analyzed for various compounds. Such compounds can include, by way of example and not limitation, water, carbon dioxide, $H_2$, sulfides, ammonia, ethanol, aldehyde, acetone, and the like. The presence of these and other compounds can be indicative of health-related issues or potential health-related issues. Once detected, information or data describing the presence or absence of these compounds can be analyzed and reported to the user. Analysis can take place either on the mobile communication device 120a or remote from the mobile communication device, as by a third-party provider.

In the latter instance, the information or data can be transmitted by the mobile communication device 120a over network 110 (FIG. 1) to the third-party provider. Once the third-party provider has analyzed the information or data, the results can then be reported back to the user and displayed on the mobile communication device 120a.

Alternately or additionally, the user's breath can be analyzed for alcohol content. In addition, in at least some embodiments, the user's breath can be analyzed to ascertain whether the user has bad breath, also known as halitosis and fetor oris. Bad breath can be associated with depression and symptoms of obsessive-compulsive disorder. Bad breath can also occur due to disorders in the nose, sinuses, throat, lungs, kidneys, esophagus, or stomach. In some rare instances, bad breath can be due to an underlying medical condition such as liver failure or ketoacidosis. As in the above example, once detected, information or data describing the presence or absence of bad breath can be analyzed and reported to the user. Analysis can take place either on the mobile communication device 120a or remote from the mobile communication device, as by a third-party provider. In the latter instance, the information or data can be transmitted by the mobile communication device 120a over network 110 (FIG. 1) to the third-party provider. Once the third-party provider has analyzed the information or data, the results can then be reported back to the user and displayed on the mobile communication device 120a. This can provide a valuable and timely diagnostic tool to enable the user to seek further medical attention in the event a bad breath condition is found.

Figure 6:
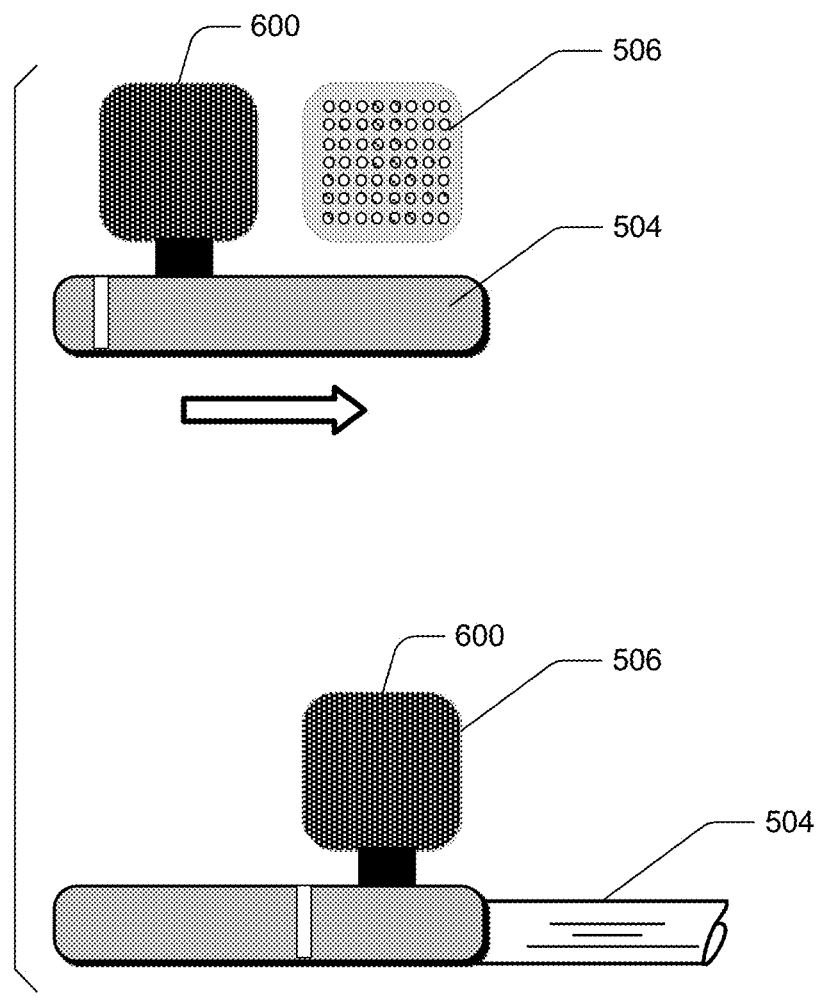
FIG. 6 illustrates an example component of a mobile communication device that accordance with one or more embodiments.

In one or more embodiments, the environment sensing inlet and fan 506 is configured take in ambient air in the environment proximate mobile communication device 120a, and use an environmental air sensor to sense one or more properties associated with the ambient air and cause analysis of the properties in a manner similar to that described above. In one or more embodiments, sensing the properties of the ambient air by the environment sensing inlet and fan 506 and corresponding environmental air sensor is conducted when the user has not deployed the deployable tube 504. To this extent, in at least some embodiments, sensing activities performed relative to the user's breath and the mobile communication device's ambient air are mutually exclusive. Accordingly, when the user has deployed the deployable tube 504, the environment sensing inlet can be blocked or otherwise disabled so that ambient air is not received by the environment sensing inlet. When the user returns the deployable tube 504 to its un-deployed position, as shown in the backside view 500, the environmental sensing inlet can be unblocked or otherwise enabled so that ambient air can now be received by the environment sensing inlet. Blocking and unblocking the environment sensing inlet can be achieved through the use of any suitable mechanism. In at least some embodiments, a mechanical coupling between the deployable tube and a blocking shield internally of the mobile communication device can enable the blocking shield to move over and cover the environment sensing inlet when the deployable tube is deployed. Likewise, when the deployable to is returned to its un-deployed position, the blocking shield can move away from and uncover the environment sensing inlet. As an example, consider FIG. 6.

There, two views of the deployable tube 504 and environment sensing inlet 506 are shown. In the top view, the deployable tube 504 is in the un-deployed position. In the bottom view, the deployable tube 504 is in the deployed position. A blocking shield 600 is mechanically coupled to and moves with the deployable tube 504. Notice that when the deployable tube is deployed, as in the bottom view, the blocking shield 600 is moved to cover the environment sensing inlet 506. When the environment sensing inlet 506 is covered, ambient air cannot be received by the inlet. Accordingly, the environmental air sensing functionality is disabled. When, however, the deployable tube 504 is placed in the un-deployed position as in the top view, the blocking shield 600 is moved to unblock the environment sensing inlet 506. When unblocked, the environment sensing inlet can receive ambient air, under the operation of the intake fan, so that the air can be processed as described above and below.

In one or more embodiments, the mobile communication device 120a, through controller 320 (FIG. 3), can process contextual information to intelligently determine when and when not to enable the environment sensing inlet and fan 506. For example, sensors on the mobile communication device can ascertain when the mobile communication device is stowed, such as by being placed in a pocket, or when the mobile communication device is placed on a table such that the environment sensing inlet and fan 506 would be blocked. For example, light sensors can be utilized to sense that the mobile communication device has been stowed in a user's pocket. Likewise, positional sensors and motion sensors can ascertain when the mobile communication device has been placed on a surface. When this occurs, the environment sensing inlet and fan 506 can be disabled. Likewise, when the mobile communication device is in use, as by a user having a telephone conference, the environment sensing inlet and fan can be disabled as well. This would prevent undesirable background noise during the user's conversation.

In at least some embodiments, one or more subscription services can be offered by third-party providers. Thus, a user may enroll in a fee-based third-party service to have the ambient air collected by the environment sensing inlet and fan 506 analyzed by way of the breath analysis module and the third-party provider. Results can then be reported back by the third-party provider to the user.

Having considered an example mobile communication device with environmental air sensing functionality, and its components in accordance with one or more embodiments, consider now an example method in accordance with one or more embodiments.

Figure 7:
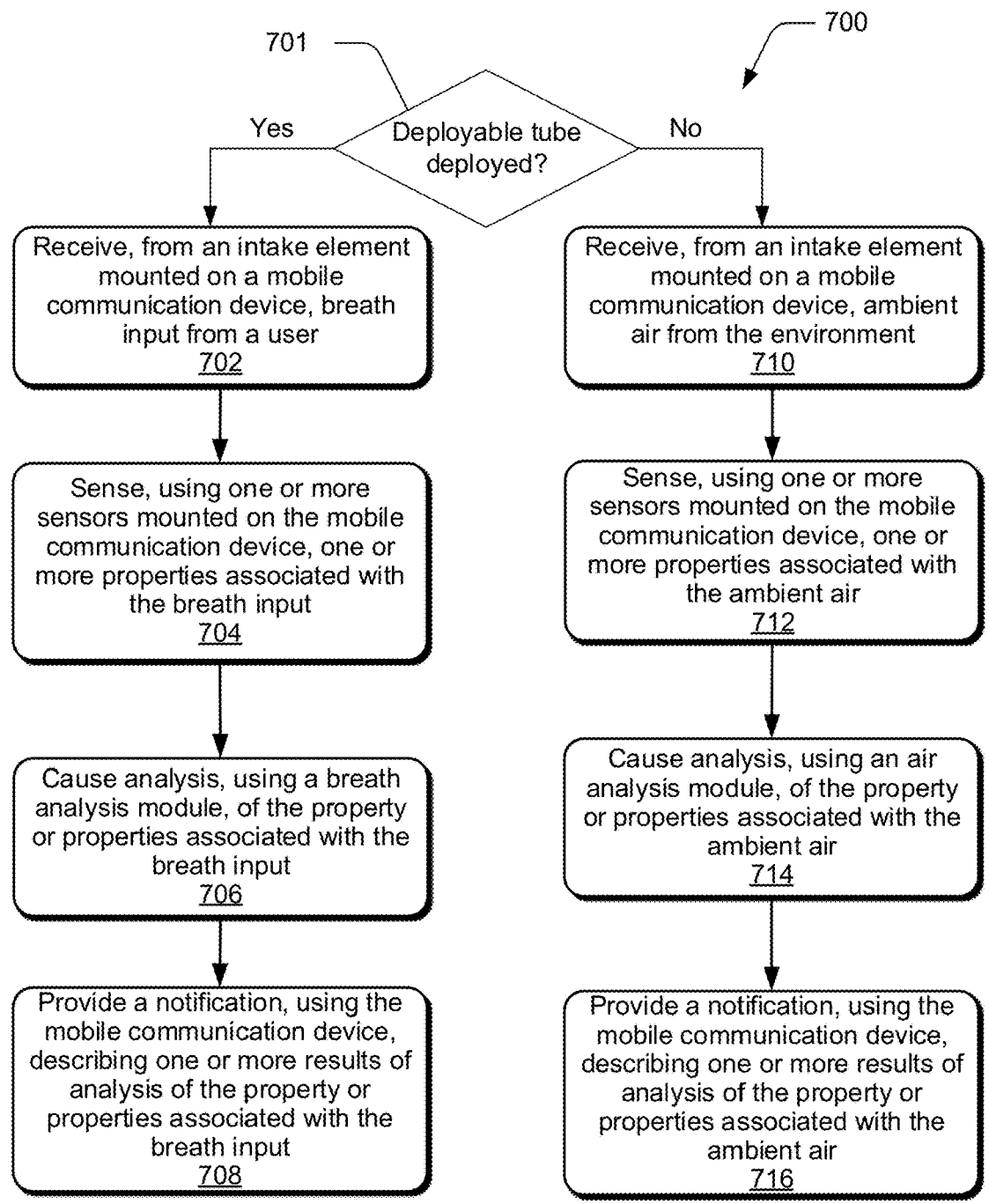
FIG. 7 is a flow diagram that illustrates operations in accordance with one or more embodiments.

FIG. 7 illustrates an example method 700 that employs breath sensory techniques, in connection with a mobile communication device, in accordance with one or more embodiments. Generally, any services, components, modules, methods, and/or operations described herein can be implemented using software, firmware, hardware (e.g., fixed logic circuitry), manual processing, or any combination thereof. Some operations of the example methods may be described in the general context of executable instructions stored on computer-readable storage memory that is local and/or remote to a computer processing system, and implementations can include software applications, programs, functions, and the like. Alternately or in addition, any of the functionality described herein can be performed, at least in part, by one or more hardware logic components, such as, and without limitation, Field-programmable Gate Arrays (FPGAs), Application-specific Integrated Circuits (ASICs), Application-specific Standard Products (ASSPs), System-on-a-chip systems (SoCs), Complex Programmable Logic Devices (CPLDs), and the like. The order in which the method is described is not intended to be construed as a limitation, and any number or combination of the described method operations can be performed in any order to perform a method, or an alternate method.

At 701, the mobile communication device determines whether the deployable tube is deployed. If the deployable tube is deployed, i.e., the "yes" branch, at 702, breath input from a user is received, from an intake element—in this case, the slidably deployable tube, mounted on a mobile communication device. Prior to receiving the breath input, the sensors on the mobile communication device can be calibrated using the humidity and temperature sensors as described above. In at least some embodiments, the slidably deployable tube can be an integral part of the mobile communication device. In at least some other embodiments, the slidably deployable tube can be part of a modular attachment that is connected to the mobile communication device. The modular attachment can be connected at any suitable location on the mobile communication device. In at least some embodiments, the modular attachment is mounted to the backside of the mobile communication device and may be held in place by magnetic coupling elements. When so mounted, components within the modular attachment can communicate with components of the mobile communication device through a suitably-configured hardware interface.

At 704, one or more properties associated with the breath input are sensed using one or more sensors mounted on the mobile communication device. Any suitable property or properties can be sensed by any suitable type of sensors. For example, properties can include, by way of example and not limitation, the constituent parts contained within or composition of the breath. Such constituent parts can include compounds, volatile compounds, volatile organic compounds, molecules, and/or constituent parts that may pertain to health-related issues. For example, the presence of certain materials in a user's breath can be indicative of certain types of cancer, such as lung cancer, esophageal cancer, tongue cancer, colorectal cancer, and the like. Further, the properties of exhaled breath may contain valuable information for users presenting with asthma, renal and liver diseases, chronic obstructive pulmonary disease, inflammatory lung disease, or metabolic disorders. Furthermore, the properties of exhaled breath may include information pertaining to chemical markers, such as acetone, which may be indicative of type I diabetes. Furthermore, the properties may include information that pertains to conditions such as lactose intolerance, fructose intolerance, various allergies, and the like. Alternately or additionally, the property or properties can include alcohol content of the breath and/or whether the user's breath can be categorized as "bad breath."

Needless to say, there are simply hundreds if not thousands of potential conditions or issues that can be identified by way of the properties associated with a user's breath. The examples provided above are intended to serve as examples only, and are not intended to limit application of the claimed subject matter.

At 706, the property or properties associated with the breath input are caused to be analyzed using, in at least some instances, a breath analysis module mounted on the mobile communication device. In yet other instances, the property or properties associated with the breath input are caused to be analyzed by transmitting information or data associated with the property or properties to a third-party provider. This can be performed by transmitting the information or data to the third-party provider using the mobile communication device.

At 708, a notification describing one or more results of analysis of the property or properties associated with the breath input is provided. The notification can include any suitable type of information that might be useful for a user. For example, the notification may simply inform the user of factual information associated with the analysis, such as the particular composition making up the user's breath. Alternately or additionally, the notification may include further information such as diagnostic information, remedial information, or recommendations such as a recommendation to seek further medical assistance as a follow-up.

The notification can be a visual notification that is displayed by the mobile communication device. Alternately or additionally, the notification can be an audible notification. In embodiments where the breath analysis takes place locally on the mobile communication device, the notification can be provided directly by the mobile communication device itself or components of or associated with the mobile communication device. In embodiments where the breath analysis takes place remotely from the mobile communication device, as by a third-party provider, the notification can be provided by receiving information from the third-party provider and providing a notification that includes the information provided by the third-party provider.

If at 701, on the other hand, the deployable tube is not deployed, i.e. the "no" branch, environmental air sensing can be enabled. When environmental air sensing is enabled and actively being employed, at 710 ambient air from the environment is received, from an intake element. Prior to receiving the ambient air, the sensors on the mobile communication device can be calibrated using the humidity and temperature sensors as described above. Any suitable type of intake element can be utilized. In the illustrated and described embodiment, an intake element in the form of an environment sensing inlet and fan 506 (FIG. 5) is employed, as described above. In at least some embodiments, the environment sensing inlet and fan 506 can be an integral part of the mobile communication device. In at least some other embodiments, the environment sensing inlet and fan 506 can be part of a modular attachment that is connected to the mobile communication device. The modular attachment can be connected at any suitable location on the mobile communication device. In at least some embodiments, the modular attachment is mounted to the backside of the mobile communication device and may be held in place by magnetic coupling elements. When so mounted, components within the modular attachment can communicate with components of the mobile communication device through a suitably-configured hardware interface.

At 712, one or more properties associated with the ambient air are sensed using one or more sensors mounted on the mobile communication device. Any suitable property or properties can be sensed by any suitable type of sensors. For example, properties can include, by way of example and not limitation, the constituent parts contained within or composition of the ambient air. Such constituent parts can include compounds, volatile compounds, volatile organic compounds, molecules, and/or constituent parts that may pertain to health-related issues. For example, the presence of certain materials in the ambient air can be indicative of certain potential health hazards.

Needless to say, there are simply hundreds if not thousands of potential conditions or issues that can be identified by way of the properties associated with ambient air. The examples provided above are intended to serve as examples only, and are not intended to limit application of the claimed subject matter.

At 714, the property or properties associated with the ambient air are caused to be analyzed using, in at least some instances, an air analysis module mounted on the mobile communication device. The air analysis module can include the breath analysis module described above. Alternately or additionally, the air analysis module may not necessarily include the breath analysis module described above. In yet other instances, the property or properties associated with the ambient air are caused to be analyzed by transmitting information or data associated with the property or properties to a third-party provider. This can be performed by transmitting the information or data to the third-party provider using the mobile communication device.

At 716, a notification describing one or more results of analysis of the property or properties associated with the ambient air is provided. The notification can include any suitable type of information that might be useful for a user. For example, the notification may simply inform the user of factual information associated with the analysis, such as the particular composition making up the ambient air. Alternately or additionally, the notification may include further information such as diagnostic information, remedial information, or recommendations such as a recommendation to move to a different location because of potentially health threatening air quality conditions.

The notification can be a visual notification that is displayed by the mobile communication device. Alternately or additionally, the notification can be an audible notification. In embodiments where the breath analysis takes place locally on the mobile communication device, the notification can be provided directly by the mobile communication device itself or components of or associated with the mobile communication device. In embodiments where the ambient air analysis takes place remotely from the mobile communication device, as by a third-party provider, the notification can be provided by receiving information from the third-party provider and providing a notification that includes the information provided by the third-party provider.

Having considered embodiments of a mobile communication device with a portable breath analyzer and environmental air sensing functionality, consider now an embodiment of a mobile communication device with a portable breath analyzer and environmental air sensing functionality which operates in an automatic mode, in accordance with one or more embodiments.

Figure 8:
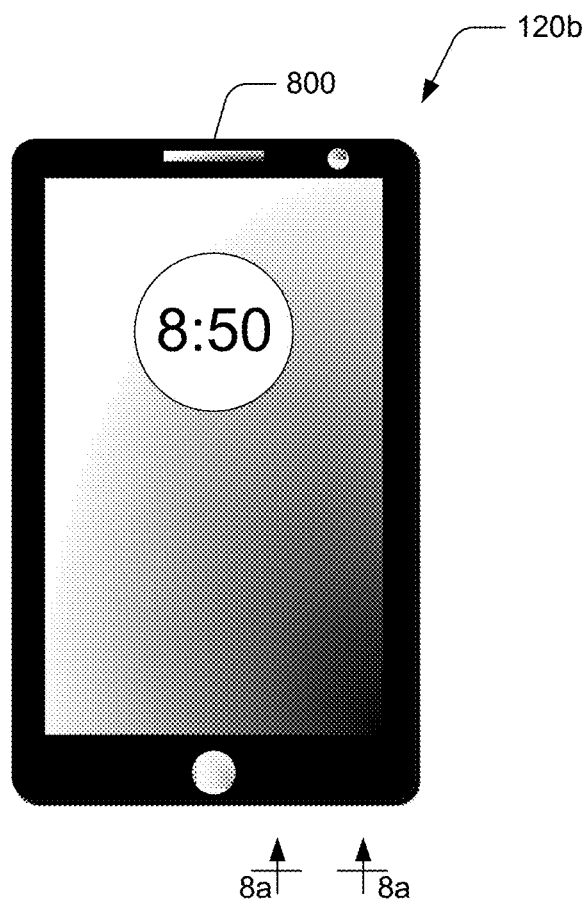
FIG. 8 illustrates an example terminal in the form of a mobile communication device in accordance with one or more embodiments.
Figure 8A:
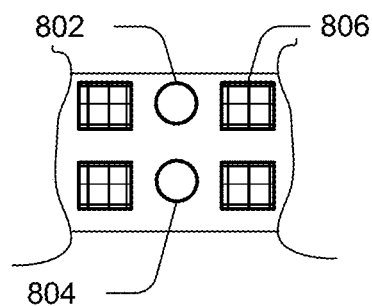
FIG. 8a is a view taken along line 8a-8a in FIG. 8, in accordance with one or more embodiments.

Mobile Communication Device with Portable Breath Analyzer and Environmental Air Sensing Functionality in Automatic Mode FIG. 8 illustrates an example terminal 120*b* in the form of a mobile communication device in accordance with one or more embodiments. A view of the frontside of the mobile communication device is shown at 800, and a bottom view is shown taken along line 8*a*-8*a* in FIG. 8*a*. In this embodiment, the mobile communication device 120*a* does not include a slidably deployable tube as in the embodiment described just above. Rather, the mobile communication device 120*a* includes a microphone 802, one or more force sensors 804, and one or more ambient air sensors one of which is labeled at 806. In this particular example, four ambient air sensors are shown distributed in a square pattern around the microphone 802 and force sensor(s) 806. The mobile communication device 120*b* includes a breath analysis module which can also serve as an ambient air sensor. Alternately, the mobile communication device can include a separate ambient air sensor. In this particular example, the mobile communication device 120*b* has two modes of operation for sensing ambient air, and the device can switch automatically between the two modes. In a first mode, corresponding to when a user is making a telephone call by speaking adjacent the mobile communication device's microphone 802, the device can automatically be placed into a breath analysis mode in which the user's breath is sensed and analyzed as described above. To ascertain that the user is on a telephone call, the mobile communication device's context can be ascertained by monitoring its calling application to ascertain whether the application is executing. Additionally, the force sensor 804 can monitor PSI conditions adjacent the force sensor and ambient air sensors 806 to ascertain whether the PSI conditions indicate that the user is talking into the mobile communication device. Furthermore, the microphone 802 can monitor for a user's voice level. So, for example, if the device's calling application is executing and other conditions, such as PSI conditions and/or voice level conditions indicate that the user is on a call, the breath analysis mode can be launched and the user's breath can be analyzed as described above.

If, on the other hand, based on the context of the mobile communication device, a determination is made that the user is not on a telephone call, a second mode can be employed in which the ambient air adjacent the device can be analyzed as described above. This can include analyzing the environmental air conditions as described just above.

When in the breath analysis mode, components of the breath analysis module, either internal to the mobile communication device 120*b* or forming part of a modular attachment to the mobile communication device 120*b*, can analyze the user's breath in one or more ways. For example, a user's breath can be analyzed for various health-related issues or potential health-related issues. For example, in at least some embodiments, the user's breath can be analyzed for various compounds. Such compounds can include, by way of example and not limitation, water, carbon dioxide, $H_2$, sulfides, ammonia, ethanol, aldehyde, acetone, and the like. The presence of these and other compounds can be indicative of health-related issues or potential health-related issues. Once detected, information or data describing the presence or absence of these compounds can be analyzed and reported to the user. Analysis can take place either on the mobile communication device 120*b* or remote from the mobile communication device, as by a third-party provider. In the latter instance, the information or data can be transmitted by the mobile communication device 120*b* over network 110 (FIG. 1) to the third-party provider. Once the third-party provider has analyzed the information or data, the results can then be reported back to the user and displayed on the mobile communication device 120*b*.

Alternately or additionally, the user's breath can be analyzed for alcohol content. In addition, in at least some embodiments, the user's breath can be analyzed to ascertain whether the user has bad breath, also known as halitosis and fetor oris. Bad breath can be associated with depression and symptoms of obsessive-compulsive disorder. Bad breath can also occur due to disorders in the nose, sinuses, throat, lungs, kidneys, esophagus, or stomach. In some rare instances, bad breath can be due to an underlying medical condition such as liver failure or ketoacidosis. As in the above example, once detected, information or data describing the presence or absence of bad breath can be analyzed and reported to the user. Analysis can take place either on the mobile communication device 120*b* or remote from the mobile communication device, as by a third-party provider. In the latter instance, the information or data can be transmitted by the mobile communication device 120*b* over network 110 (FIG. 1) to the third-party provider. Once the third-party provider has analyzed the information or data, the results can then be reported back to the user and displayed on the mobile communication device 120*b*. This can provide a valuable and timely diagnostic tool to enable the user to seek further medical attention in the event a bad breath condition is found.

In one or more embodiments, when in the second mode in which the environmental air or ambient air adjacent the mobile communication device is sensed, the ambient air sensors 806 are configured to sense one or more properties associated with the ambient air and cause analysis of the properties in a manner similar to that described above. In one or more embodiments, sensing the properties of the ambient air by the ambient air sensors 806 is conducted when the user is not on a call, as described above, and the mobile communication device is not stowed or placed in a manner which obscures the microphone and ambient air sensors. To this extent, in at least some embodiments, sensing activities performed relative to the user's breath and the mobile communication device's ambient air are mutually exclusive. Accordingly, when the user is not on a telephone call, and the device is not stowed or placed in a manner which blocks the microphone 802 and ambient air sensors 806, ambient air sensors 806 can sense that ambient air and cause analysis thereof to be performed as described above. If, on the other hand, the user is on a telephone call as ascertained by the various sensors on the mobile communication device, breath analysis can be automatically conducted as described above.

In one or more embodiments, the mobile communication device 120*b*, through controller 320 (FIG. 3) can process contextual information to intelligently determine when and when not to place the device into a particular air sensing mode. For example, sensors on the mobile communication device can ascertain when the mobile communication device is stowed, such as by being placed in a pocket, or when the mobile communication device is placed on a table such that the ambient air sensors would be blocked. For example, light sensors can be utilized to sense that the mobile communication device has been stowed in a user's pocket. Likewise, positional sensors and motion sensors can ascertain when the device has been placed on a surface. When this occurs, the ambient air sensing mode can be disabled. Likewise, when the mobile communication device is in use, as by a user having a telephone call, the ambient air sensing which senses the environmental air adjacent the device can be disabled in favor of conducting breath analysis for the user.

In at least some embodiments, one or more subscription services can be offered by third-party providers. Thus, a user may enroll in a fee-based third-party service to have the ambient air/user's breath collected and analyzed by way of the breath analysis module and the third-party provider. Results can then be reported back by the third-party provider to the user.

Having considered an example mobile communication device with environmental air sensing functionality, and its components in accordance with one or more embodiments, consider now an example method in accordance with one or more embodiments.

Figure 9:
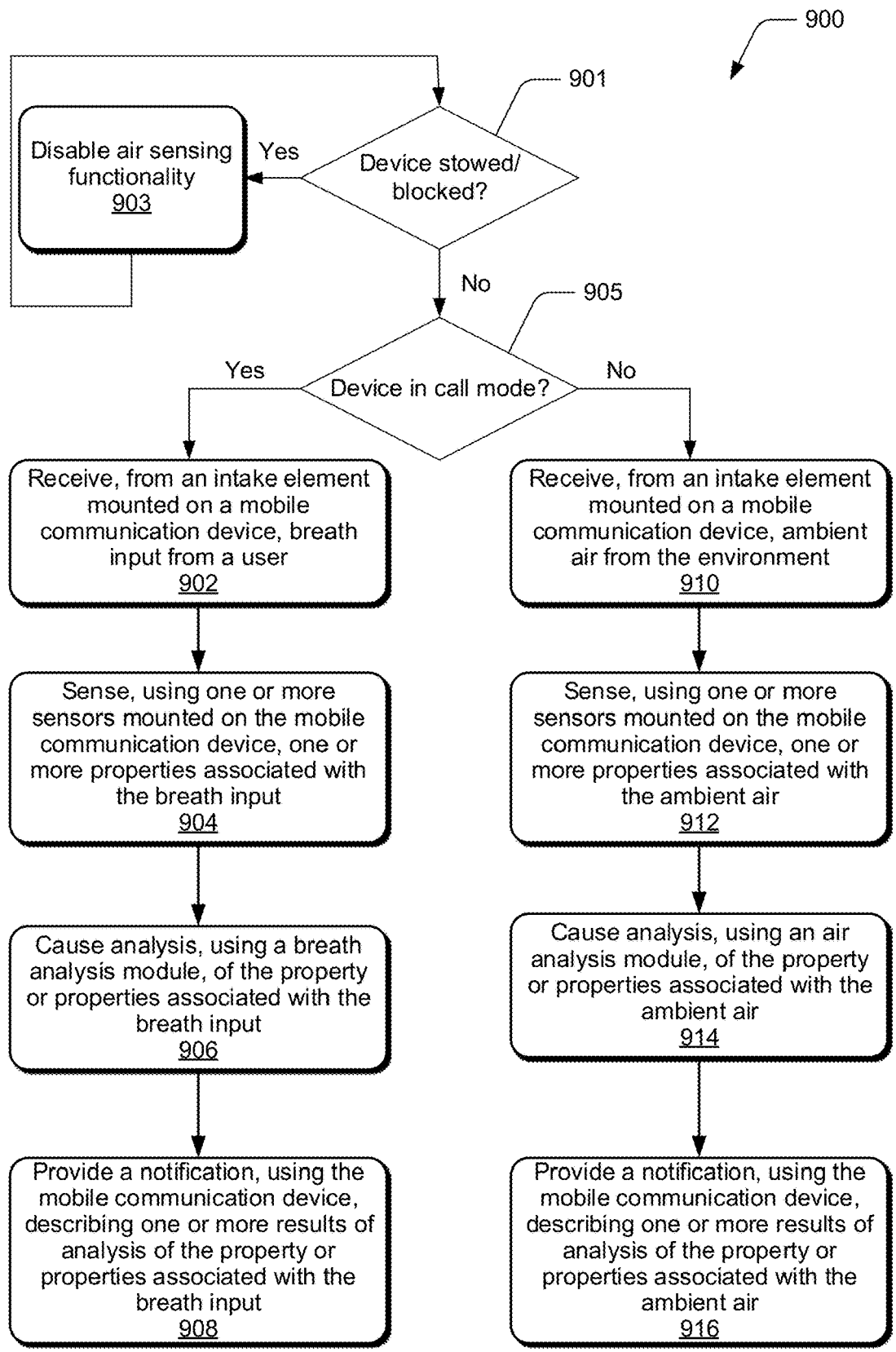
FIG. 9 is a flow diagram that illustrates operations in accordance with one or more embodiments.

FIG. 9 illustrates an example method 900 that employs breath sensory techniques, in connection with a mobile communication device, in accordance with one or more embodiments. Generally, any services, components, modules, methods, and/or operations described herein can be implemented using software, firmware, hardware (e.g., fixed logic circuitry), manual processing, or any combination thereof. Some operations of the example methods may be described in the general context of executable instructions stored on computer-readable storage memory that is local and/or remote to a computer processing system, and implementations can include software applications, programs, functions, and the like. Alternately or in addition, any of the functionality described herein can be performed, at least in part, by one or more hardware logic components, such as, and without limitation, Field-programmable Gate Arrays (FPGAs), Application-specific Integrated Circuits (ASICs), Application-specific Standard Products (ASSPs), System-on-a-chip systems (SoCs), Complex Programmable Logic Devices (CPLDs), and the like. The order in which the method is described is not intended to be construed as a limitation, and any number or combination of the described method operations can be performed in any order to perform a method, or an alternate method.

At 901, the mobile communication device determines whether the mobile communication device is stowed or otherwise blocked. The mobile communication device can be considered as blocked if its ambient air sensors are blocked. If the device is stowed and/or blocked, i.e. the "yes" branch, at 903 the air sensing functionality of the device is disabled. This includes disabling both the breath analysis mode and the ambient air sensing mode. The method can then return to 901 to ascertain whether the mobile communication device remains stowed or blocked. If, on the other hand, at 901 the mobile communication device is not stowed and/or blocked, i.e., the "no" branch, a determination is made at 905 as to whether the mobile communication device is in a call mode, so as to correspond to a situation where the device's user is making a call. This step can be performed in any suitable way including, by way of example and not limitation, monitoring whether a call application is executing, monitoring corresponding force sensors, such as force sensor 804 for PSI conditions, and/or monitoring the device's microphone for a user's voice level. If the device is in the call mode, i.e., the "yes" branch, the breath analysis mode can be enabled and can branch to 902. If, on the other hand, the device is not in call mode, i.e., the "no" branch and is not stowed or blocked, the ambient air analysis mode can be enabled and can branch to 910. In one or more embodiments, the sensors on the mobile communication device can be calibrated using the humidity and temperature sensors as described above. In this particular instance, if and when the device is placed into the call mode, the sensors can be initially calibrated before or during placement of the call. For example, when a user launches the call application, an initial calibration can be triggered. Alternately, if the device is not in the call mode and is not stowed or blocked, the sensors can be periodically calibrated. Alternately, the sensors can be calibrated upon the occurrence of an event, such as the user ending a call and the force sensors sensing that the user is no longer speaking into the device.

In the breath analysis mode, at 902, breath input from a user is received, from an intake element—in this case, the ambient air sensors 806 (FIG. 8*a*), mounted on a mobile communication device. In at least some embodiments, the ambient air sensors can be an integral part of the mobile communication device, such as by being mounted on one of the sides of the device. In at least some other embodiments, the ambient air sensors can be part of a modular attachment that is connected to the mobile communication device. The modular attachment can be connected at any suitable location on the mobile communication device. In at least some embodiments, the modular attachment is mounted to the backside of the mobile communication device and may be held in place by magnetic coupling elements. When so mounted, components within the modular attachment can communicate with components of the mobile communication device through a suitably-configured hardware interface.

At 904, one or more properties associated with the breath input are sensed using one or more sensors mounted on the mobile communication device. Any suitable property or properties can be sensed by any suitable type of sensors. For example, properties can include, by way of example and not limitation, the constituent parts contained within or composition of the breath. Such constituent parts can include compounds, volatile compounds, volatile organic compounds, molecules, and/or constituent parts that may pertain to health-related issues. For example, the presence of certain materials in a user's breath can be indicative of certain types of cancer, such as lung cancer, esophageal cancer, tongue cancer, colorectal cancer, and the like. Further, the properties of exhaled breath may contain valuable information for users presenting with asthma, renal and liver diseases, chronic obstructive pulmonary disease, inflammatory lung disease, or metabolic disorders. Furthermore, the properties of exhaled breath may include information pertaining to chemical markers, such as acetone, which may be indicative of type I diabetes. Furthermore, the properties may include information that pertains to conditions such as lactose intolerance, fructose intolerance, various allergies, and the like. Alternately or additionally, the property or properties can include alcohol content of the breath and/or whether the user's breath can be categorized as "bad breath."

Needless to say, there are simply hundreds if not thousands of potential conditions or issues that can be identified by way of the properties associated with a user's breath. The examples provided above are intended to serve as examples only, and are not intended to limit application of the claimed subject matter.

At 906, the property or properties associated with the breath input are caused to be analyzed using, in at least some instances, a breath analysis module mounted on the mobile communication device. In yet other instances, the property or properties associated with the breath input are caused to be analyzed by transmitting information or data associated with the property or properties to a third-party provider. This can be performed by transmitting the information or data to the third-party provider using the mobile communication device.

At 908, a notification describing one or more results of analysis of the property or properties associated with the breath input is provided. The notification can include any suitable type of information that might be useful for a user. For example, the notification may simply inform the user of factual information associated with the analysis, such as the particular composition making up the user's breath. Alternately or additionally, the notification may include further information such as diagnostic information, remedial information, or recommendations such as a recommendation to seek further medical assistance as a follow-up.

The notification can be a visual notification that is displayed by the mobile communication device. Alternately or additionally, the notification can be an audible notification. In embodiments where the breath analysis takes place locally on the mobile communication device, the notification can be provided directly by the mobile communication device itself or components of or associated with the mobile communication device. In embodiments where the breath analysis takes place remotely from the mobile communication device, as by a third-party provider, the notification can be provided by receiving information from the third-party provider and providing a notification that includes the information provided by the third-party provider.

If, on the other hand, the mobile communication device is not stowed/blocked at 901 or in the call mode at 905, the ambient air analysis module can be enabled to perform environmental air sensing. When environmental air sensing is enabled and actively being employed, at 910 ambient air from the environment is received, from an intake element. Any suitable type of intake element can be utilized. In the illustrated and described embodiment, an intake element in the form of one or more ambient air sensors 806 (FIG. 8a) is employed, as described above. In at least some embodiments, the ambient air sensors can be an integral part of the mobile communication device. In at least some other embodiments, the ambient air sensors can be part of a modular attachment that is connected to the mobile communication device. The modular attachment can be connected at any suitable location on the mobile communication device. In at least some embodiments, the modular attachment is mounted to the backside of the mobile communication device and may be held in place by magnetic coupling elements. When so mounted, components within the modular attachment can communicate with components of the mobile communication device through a suitably-configured hardware interface.

At 912, one or more properties associated with the ambient air are sensed using one or more sensors mounted on the mobile communication device. Any suitable property or properties can be sensed by any suitable type of sensors. For example, properties can include, by way of example and not limitation, the constituent parts contained within or composition of the ambient air. Such constituent parts can include compounds, volatile compounds, volatile organic compounds, molecules, and/or constituent parts that may pertain to health-related issues. For example, the presence of certain materials in the ambient air can be indicative of certain potential health hazards.

Needless to say, there are simply hundreds if not thousands of potential conditions or issues that can be identified by way of the properties associated with ambient air. The examples provided above are intended to serve as examples only, and are not intended to limit application of the claimed subject matter.

At 914, the property or properties associated with the ambient air are caused to be analyzed using, in at least some instances, an air analysis module mounted on the mobile communication device. The air analysis module can include the breath analysis module described above. Alternately or additionally, the air analysis module may not necessarily include the breath analysis module described above. In yet other instances, the property or properties associated with the ambient air are caused to be analyzed by transmitting information or data associated with the property or properties to a third-party provider. This can be performed by transmitting the information or data to the third-party provider using the mobile communication device.

At 916, a notification describing one or more results of analysis of the property or properties associated with the ambient air is provided. The notification can include any suitable type of information that might be useful for a user. For example, the notification may simply inform the user of factual information associated with the analysis, such as the particular composition making up the ambient air. Alternately or additionally, the notification may include further information such as diagnostic information, remedial information, or recommendations such as a recommendation to move to a different location because of potentially health threatening air quality conditions.

The notification can be a visual notification that is displayed by the mobile communication device. Alternately or additionally, the notification can be an audible notification. In embodiments where the breath analysis takes place locally on the mobile communication device, the notification can be provided directly by the mobile communication device itself or components of or associated with the mobile communication device. In embodiments where the ambient air analysis takes place remotely from the mobile communication device, as by a third-party provider, the notification can be provided by receiving information from the third-party provider and providing a notification that includes the information provided by the third-party provider.

Having considered an example method in accordance with one or more embodiments, consider now an example computing device that can implement the embodiments described above.

Example Device

Figure 10:
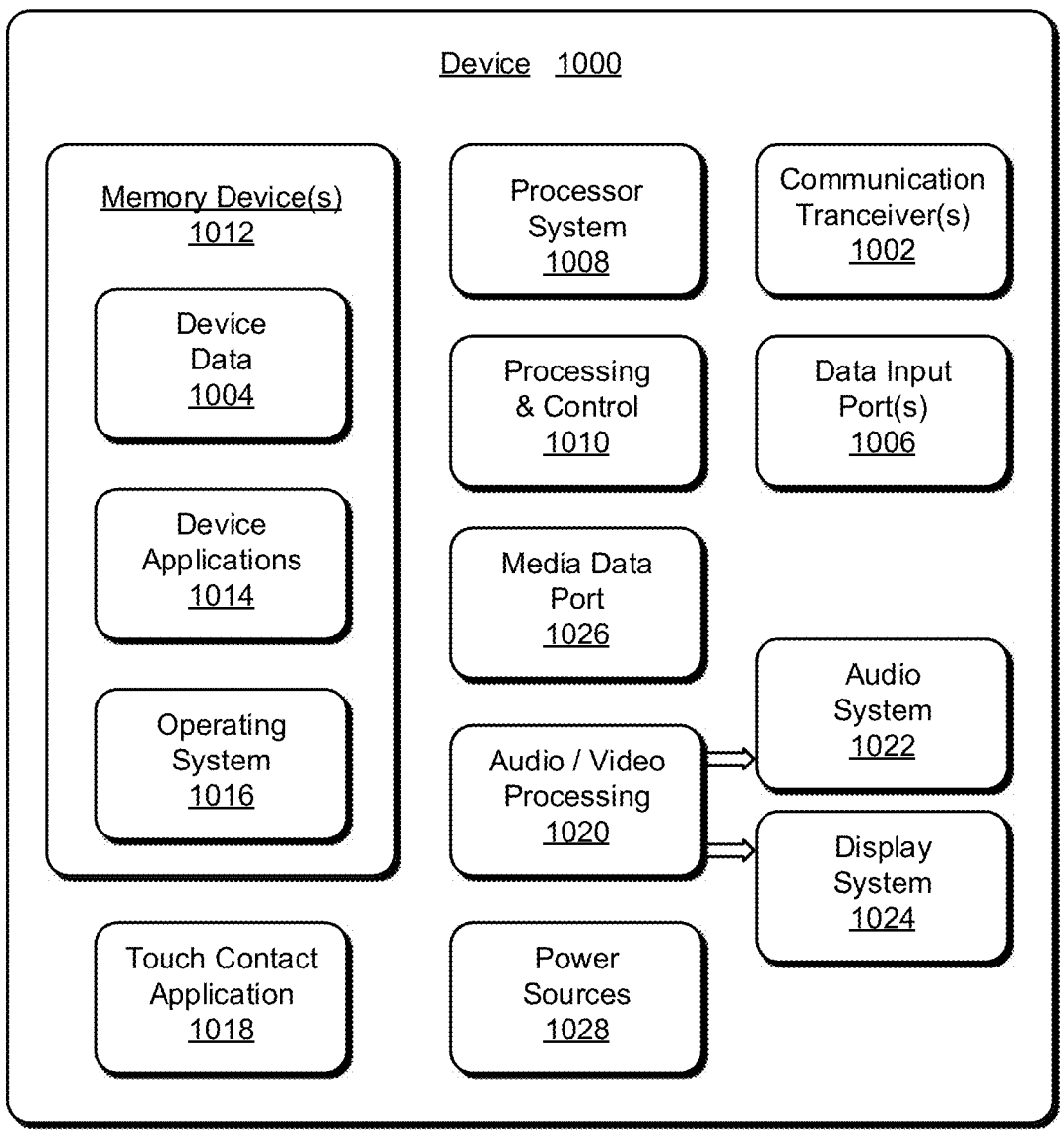
FIG. 10 illustrates various components of an example device that can implement various embodiments.

FIG. 10 illustrates various components of an example mobile communication device 1000 in which breath sensory and environmental air sensing embodiments can be implemented. The example device 1000 can be implemented as any suitable type of computing device, such as any type of client device, mobile phone, tablet, computing, communication, entertainment, gaming, media playback, and/or other type of device such as those mentioned above. For example, the device 120 shown in FIG. 1 may be implemented as the example device 1000.

The device 1000 includes communication transceivers 1002 that enable wired and/or wireless communication of device data 1004 with other devices. Additionally, the device data can include any type of audio, video, and/or image data. Example transceivers include wireless personal area network (WPAN) radios compliant with various IEEE 802.15 (Bluetooth™) standards, wireless local area network (WLAN) radios compliant with any of the various IEEE 802.11 (WiFi™) standards, wireless wide area network (WWAN) radios for cellular phone communication, wireless metropolitan area network (WMAN) radios compliant with various IEEE 802.15 (WiMAX™) standards, and wired local area network (LAN) Ethernet transceivers for network data communication.

The device 1000 may also include one or more data input ports 1006 via which any type of data, media content, and/or inputs can be received, such as user-selectable inputs to the device, messages, music, television content, recorded content, and any other type of audio, video, and/or image data received from any content and/or data source. The data input ports may include USB ports, coaxial cable ports, and other serial or parallel connectors (including internal connectors) for flash memory, DVDs, CDs, and the like. These data input ports may be used to couple the device to any type of components, peripherals, or accessories such as microphones and/or cameras.

The device 1000 includes a processing system 1008 of one or more processors (e.g., any of microprocessors, controllers, and the like) and/or a processor and memory system implemented as a system-on-chip (SoC) that processes computer-executable instructions. The processor system may be implemented at least partially in hardware, which can include components of an integrated circuit or on-chip system, an application-specific integrated circuit (ASIC), a field-programmable gate array (FPGA), a complex programmable logic device (CPLD), and other implementations in silicon and/or other hardware. Alternatively, or in addition, the device can be implemented with any one or combination of software, hardware, firmware, or fixed logic circuitry that is implemented in connection with processing and control circuits, which are generally identified at 1010. Processor system 1008 can also include various sensors such as those described above, as well as one or more ambient air analysis modules, such as breath analysis module 396 (FIG. 3) and any of the components described in relation to any of the embodiments discussed herein. The device 1000 may further include any type of a system bus or other data and command transfer system that couples the various components within the device. A system bus can include any one or combination of different bus structures and architectures, as well as control and data lines.

The device 1000 also includes computer-readable storage memory or memory devices 1012 that enable data storage, such as data storage devices that can be accessed by a computing device, and that provide persistent storage of data and executable instructions (e.g., software applications, programs, functions, and the like). Examples of the computer-readable storage memory 1012 include volatile memory and non-volatile memory, fixed and removable media devices, and any suitable memory device or electronic data storage that maintains data for computing device access. The computer-readable storage memory can include various implementations of random access memory (RAM), read-only memory (ROM), flash memory, and other types of storage media in various memory device configurations. The device 1000 may also include a mass storage media device.

The computer-readable storage memory provides data storage mechanisms to store the device data 1004, other types of information and/or data, and various device applications 1014 (e.g., software applications). For example, an operating system 1016 can be maintained as software instructions with a memory device and executed by the processing system 1008. The device applications may also include a device manager, such as any form of a control application, software application, signal-processing and control module, code that is native to a particular device, a hardware abstraction layer for a particular device, and so on. In this example, the device 1000 includes a touch contact application 1018.

The device 1000 also includes an audio and/or video processing system 1020 that generates audio data for an audio system 1022 and/or generates display data for a display system 1024. The audio system and/or the display system may include any devices that process, display, and/or otherwise render audio, video, display, and/or image data. Display data and audio signals can be communicated to an audio component and/or to a display component via an RF (radio frequency) link, S-video link, HDMI (high-definition multimedia interface), composite video link, component video link, DVI (digital video interface), analog audio connection, or other similar communication link, such as media data port 1026. In implementations, the audio system and/or the display system are integrated components of the example device. Alternatively, the audio system and/or the display system are external, peripheral components to the example device.

The device 1000 can also include one or more power sources 1028, such as when the device is implemented as a mobile device. The power sources may include a charging and/or power system, and can be implemented as a flexible strip battery, a rechargeable battery, a charged super-capacitor, and/or any other type of active or passive power source.

CONCLUSION

Various embodiments provide a mobile communication device, such as a mobile communication device, with functions including telecommunications capabilities, breath sensory functions and, in some instances, environmental air sensing functions. The breath sensory functions can be used to measure alcohol levels, as well as to detect properties that pertain to various health conditions and issues. The environmental air sensing functions can, in at least some embodiments, be provided along with the breath sensory functions. In at least some embodiments, the environmental air sensing functions and the breath sensory functions can be selected by a user. For example, the user may opt to enable the breath sensory functions and then, may opt to switch to the environmental air sensing functions. In other embodiments, the environmental air sensing functions and the breath sensory functions can be automatically selected depending on a context associated with the mobile communication device. That is, the mobile communication device can determine a particular context, such as whether or not the user is on a telephone call, and can automatically select and enable the breath sensory functions. Alternately, the mobile communication device can determine when the user is not on a telephone call and the mobile communication device is in a state in which the environmental air sensing functions can be enabled. In these instances, the environmental air sensing functions can be automatically selected and enabled by the device. Of course, the user can be provided with the notification that the environmental air sensing functions are available and can be given the choice as to whether enable the functions or not.

Although breath sensory and environmental air sensing embodiments have been described in language specific to features and/or methods, the subject of the appended claims is not necessarily limited to the specific features or methods described. Rather, the specific features and methods are disclosed as example implementations, and other equivalent features and methods are intended to be within the scope of the appended claims. Further, various different embodiments are described and it is to be appreciated that each described embodiment can be implemented independently or in connection with one or more other described embodiments.

The invention claimed is:

1. A method for performing breath analysis implemented by a mobile communication device, the method comprising:
   receiving, via an intake element of the mobile communication device, breath input from a user, the intake element being separate from an environment sensing inlet for receiving ambient air;
   determining that the mobile communication device is operating in a call mode, and responsive to the mobile communication device operating in the call mode:
      disabling the environment sensing inlet of the mobile communication device; and
      enabling one or more sensors of the mobile communication device to sense one or more properties associated with the breath input;
   analyzing the one or more properties associated with the breath input using a breath analysis module; and
   providing a notification describing one or more results of the analyzing the one or more properties associated with the breath input.

2. The method as recited in claim 1, wherein the one or more properties include alcohol content associated with the breath input.

3. The method as recited in claim 1, wherein the one or more properties pertain to health-related issues.

4. The method as recited in claim 1, wherein the analyzing the one or properties comprises transmitting data associated with the one or more properties to a third-party provider.

5. The method as recited in claim 4, further comprising:
receiving analysis information from the third-party provider and providing the analysis information received from the third-party provider to the user.

6. The method as recited in claim 1, further comprising:
determining humidity data and temperature data of an environment around the mobile communication device;
calibrating a gas baseline based on the humidity data and the temperature data; and
wherein the receiving the breath input is based on the calibrated gas baseline.

7. The method as recited in claim 1, further comprising:
determining humidity data and temperature data of an environment around the mobile communication device; and
calibrating the one or more sensors based on at least one of the humidity data or the temperature data.

8. A mobile device comprising:
an intake element that receives breath input from a user of the mobile device, the intake element being separate from an environment sensing inlet for receiving ambient air from an environment around the mobile device;
one or more sensors for sensing one or more properties associated with the breath input;
a breath analysis module implemented at least partially in computer hardware and configured to:
  determine that the mobile device is operating in a call mode, and responsive to the mobile device operating in the call mode:
    disable the environment sensing inlet; and
    enable the one or more sensors to sense the one or more properties associated with the breath input;
  analyze the one or more properties associated with the breath input; and
  generate a notification of analysis results of the one or more properties associated with the breath input.

9. The mobile device as recited in claim 8, wherein the intake element, the one or more sensors, and the breath analysis module comprise part of a modular attachment that is detachably connected to the mobile device.

10. The mobile device as recited in claim 8, wherein the one or more properties include alcohol content associated with the breath input.

11. The mobile device as recited in claim 8, wherein the one or more properties pertain to health-related issues.

12. The mobile device as recited in claim 8, wherein the breath analysis module is configured to initiate the one or more properties associated with the breath input being analyzed by transmitting data associated with the one or more properties to a third-party provider.

13. The mobile device as recited in claim 12, wherein the breath analysis module is configured to:
receive the analysis results from the third-party provider; and
provide the notification of the analysis results received from the third-party provider to the user.

14. The mobile device as recited in claim 8, wherein the one or more sensors are calibrated based on humidity data or temperature data of the environment around the mobile device responsive to the call mode of the mobile device being ended.

15. The mobile device as recited in claim 8, wherein the one or more sensors are calibrated based on humidity data or temperature data of the environment around the mobile device responsive to a call application being initiated on the mobile device to operate in the call mode.

16. The mobile device as recited in claim 8, wherein the one or more sensors are periodically calibrated based on humidity data or temperature data of the environment around the mobile device.

17. A mobile device comprising:
a modular attachment configured to be detachably connected to the mobile device, the modular attachment including an intake element that receives breath input from a user of the mobile device, the intake element being separate from an environment sensing inlet for receiving ambient air;
one or more sensors mounted on the modular attachment for sensing one or more properties associated with the breath input;
a breath analysis module of the modular attachment implemented at least partially in computer hardware and configured to:
  determine that the mobile device is operating in a call mode, and responsive to the mobile device operating in the call mode:
    disable the environment sensing inlet; and
    enable the one or more sensors to sense the one or more properties associated with the breath input;
  analyze the one or more properties associated with the breath input; and
  generate a notification of analysis results of the one or more properties associated with the breath input.

18. The mobile device as recited in claim 17, wherein the one or more properties include alcohol content associated with the breath input.

19. The mobile device as recited in claim 17, wherein the one or more properties pertain to health-related issues.

20. The mobile device as recited in claim 17, wherein the notification includes a recommendation to the user.

* * * * *